(12) United States Patent
Pellicier et al.

(10) Patent No.: US 9,480,637 B2
(45) Date of Patent: Nov. 1, 2016

(54) USE OF A CEREAL EXTRACT AS A SLIMMING ACTIVE AGENT IN A SLIMMING COSMETIC COMPOSITION

(75) Inventors: Françoise Pellicier, Loury (FR); Jean-Christophe Archambault, Meung sur Loire (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 417 days.

(21) Appl. No.: 12/658,275

(22) Filed: Feb. 10, 2010

(65) Prior Publication Data

US 2010/0316745 A1 Dec. 16, 2010

(30) Foreign Application Priority Data

Jun. 10, 2009 (FR) ...................................... 09 53838

(51) Int. Cl.
*A61K 36/889* (2006.01)
*A61K 8/97* (2006.01)
*A61K 36/899* (2006.01)
*A61Q 19/06* (2006.01)

(52) U.S. Cl.
CPC ............... *A61K 8/97* (2013.01); *A61K 36/899* (2013.01); *A61Q 19/06* (2013.01)

(58) Field of Classification Search
None
See application file for complete search history.

(56) References Cited

U.S. PATENT DOCUMENTS

| 5,709,864 | A * | 1/1998 | Andre et al. ................... 424/776 |
| 7,507,731 | B2 * | 3/2009 | Rosenfeld et al. ......... 514/230.5 |
| 2004/0142007 | A1 * | 7/2004 | Moussou et al. ............. 424/401 |
| 2008/0287552 | A1 * | 11/2008 | Paufique ....................... 514/777 |

FOREIGN PATENT DOCUMENTS

| EP | 0 486 595 B1 | 5/1992 |
| EP | 0 711 141 B1 | 5/1996 |
| FR | 2 893 504 A1 | 5/2007 |
| WO | WO 91/02516 | 3/1991 |

OTHER PUBLICATIONS

Autio (Journal of the Institute of Brewing (2001), vol. 107, No. 1, pp. 19-25).*
Sastry et al., "Quantitative changes in integrin and focal adhesion signaling regulate myoblast cell cycle withdrawl," *J. Cell. Biol.* (1999) 144 (6): 1295-1309.
Green et al., "Spontaneous heritable changes leading to increased adipose conversion in 3T3 cells," *Cell* (1976) 7:105-113.
Kuwada et al., "Integrin α5/β1 mediates fibornectin-dependent epithelial cell proliferation through epidermal growth factor receptor activation," *Molecular Biology of the Cell* (2000) 11 (7): 2485-2496.
Liu et al., "Changes in integrin expression during adipocyte differentiation," *Cell Metabolism* (2005): 165-177.

* cited by examiner

*Primary Examiner* — Susan Hoffman
(74) *Attorney, Agent, or Firm* — Merchant & Gould P.C.

(57) ABSTRACT

A cereal extract is cosmetically used and obtained by at least one polar solvent. This cereal extract is used as a slimming agent in a slimming cosmetic composition. The cosmetic use makes it possible to achieve an effective slimming cosmetic care with a natural, nontoxic slimming agent.

33 Claims, 2 Drawing Sheets
(2 of 2 Drawing Sheet(s) Filed in Color)

0.05% RYE EXTRACT TREATMENT

USE OF A CEREAL EXTRACT AS A SLIMMING ACTIVE AGENT IN A SLIMMING COSMETIC COMPOSITION

BACKGROUND OF THE INVENTION

1. Field of the Invention

The present invention relates to a novel use of a cereal extract as a slimming active agent in a slimming cosmetic composition, and also to a cosmetic care method using said composition.

2. Prior Art

Adipose tissue plays a central role in controlling the energy balance of the organism. It is constituted of aggregate cells, adipocytes, and of an abundant connective-vascular stroma. Adipocytes (or adipose cells) can either store energy in lipid form (essentially triglycerides), or release this energy into the extracellular medium in the form of fatty acids and glycerol. To do this, the adipocyte contains an enormous lipid vacuole, which is approximately 80% of the cell mass.

These lipids are placed in reserve by esterification of fatty acids in the form of triacylglycerols (lipogenesis). The latter can be hydrolyzed by triglyceride lipase, thereby allowing these fatty acids to be released into the blood stream (lipolysis).

Mature adipocytes, located in the hypodermis, are formed from adipocyte precursors, or preadipocytes, which are fibroblast-type cells that can differentiate into adipocytes in the adipose tissue. After a growth phase, the preadipocyte experiences a pause in cell multiplication. It then enters into the process of adipocyte differentiation.

During terminal differentiation, adipocytes exhibit a considerable lipogenic capacity. This results in the gradual accumulation, in the cytoplasm, of lipid vacuoles which will subsequently fuse. This step is up- or down-regulated by factors in the surrounding medium, such as hormones, cytokines, growth factors or vitamins.

The adipocyte differentiation process is also accompanied by changes in the nature of the expression and in the composition of cell surface proteins known as "integrins".

These integrins each have a large extracellular segment, a transmembrane segment and a cytoplasmic segment which is generally very short and devoid of enzymatic activity.

The integrins can be likened to receptors for molecules that make up the connective tissue. They represent a family of heterodimers located at the surface of cells and each composed of an α-subunit and of a β-subunit which are noncovalently associated: fourteen isoforms are known for the α-chain and nine isoforms are known for the β-chain. These α and β isoforms associate with one another in various ways so as to give rise to more than 20 receptors, which confers great diversity on the system.

The integrins are involved in intercellular adhesion and cell-extracellular matrix protein (laminin, fibronectin, collagen, vitronectin, etc.) adhesion. Inside cells, the cytoplasmic segment of the integrins is associated with varied proteins of the cytoskeleton, such as talin or α-actinin. The transmembrane segment not only promotes the regulation of adhesion, but also makes it possible to transmit intracellular signals which can modify the behavior of the cell (stationary state, migratory state, proliferation, secretion, etc.).

The integrins also have a role in transduction signals and gene regulation. It has been shown that the α5 and α6 integrins, which are respectively receptors for fibronectin and for laminin, act reciprocally to regulate proliferation and differentiation of preadipocytes into adipocytes (Liu J et al., *Cell Metab.* 2005 September; 2(3):165-77). The authors have shown that the more α5 integrin is expressed, the less the cells enter into differentiation. The α5 subunit is greatly expressed in preadipocytes but is undetectable in adipocytes; conversely, the α6 subunit is undetectable in preadipocytes and abundant in adipocytes.

Cells which overexpress α5 integrin maintain a fibroblast phenotype with few lipid droplets. The overexpression of α6 integrin in cells, 5 days after induction of cell differentiation, induces the synthesis of intracellular triglycerides.

A switch in integrin protein expression thus takes place during the adipocyte differentiation process, between α5 integrins, which keep the cells in an undifferentiated state (preadipocytes) and α6 integrins, which "control" the signaling process leading to terminal differentiation into adipocytes.

FR 2 893 504 (SILAB) discloses an extract of cereals and/or of legumes, said extract being obtained in an aqueous medium. This extract is used as an active agent in cosmetic compositions for obtaining an anti-aging, and in particular antiwrinkle, effect.

FR 2 893 504 does not suggest, for this extract, any effect with respect to integrin expression in the cells of the adipose tissue of the skin, and does not envision, for this extract, any use as a slimming active agent in cosmetic compositions.

SUMMARY OF THE INVENTION

The main objective of the invention is to solve the new technical problem consisting of the provision of a novel slimming agent using a renewable natural source which is biocompatible, which has no toxicity, and which is simple to prepare by means of an industrial preparation process without there being any limit in terms of amounts.

This technical problem is solved for the first time by the present invention in a simple, inexpensive manner that can be used on the industrial and cosmetic scale.

BRIEF DESCRIPTION OF THE FIGURES

This patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
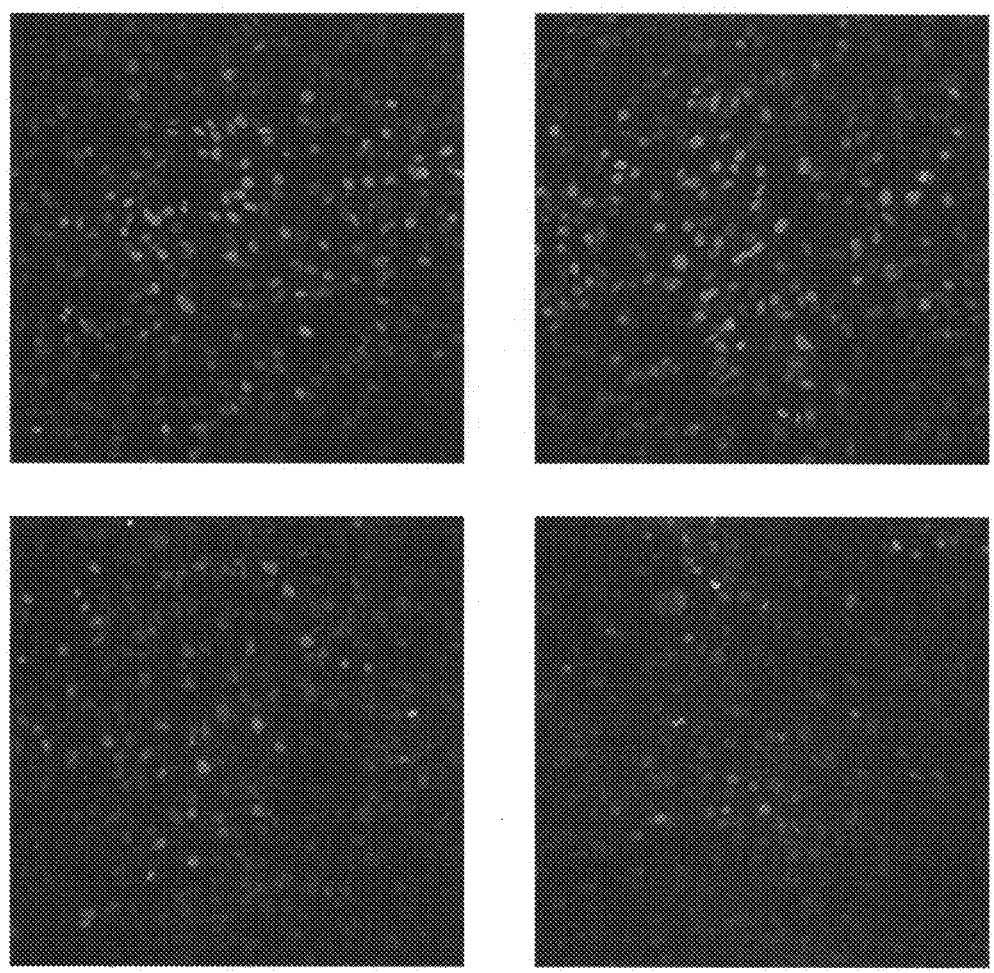
FIG. 1 represents four images taken on four different areas of the culture medium of nontreated control cells, to be analyzed according to the method described in example 2, paragraph 4 hereinafter, in the context of the immunolabeling for the detection of cell nuclei and of the expression of the network of α5 integrins at the surface of nontreated control cells.

The subject of the present invention is thus a novel use of a cereal extract notably obtained by means of at least one polar solvent, as a slimming agent in a cosmetic composition.

According to one particular embodiment, the extract is obtained from all or part of a cereal alone or as a mixture with at least one other cereal.

According to another particular embodiment, the cereal is a cereal rich in saccharide compounds, in particular rich in xylan or in at least one xylan derivative such as an arabinoxylan, in particular constituted of a backbone of D-xylopyranose to which at least one [alpha]-L-arabino-furanose group is linked in a [beta]-(1-4) linkage.

According to another particular embodiment, the cereal is chosen from wheat, rye, barley or alternatively oats.

According to yet another particular embodiment, the cereal extract is obtained from at least one cereal fraction chosen from the fibers, in particular those contained in the stalks or the leaves, the seeds, the hulls or else the bran of cereals, or else from flakes of said cereal. According to one variant embodiment, said flakes may themselves be obtained from seeds of cereals having undergone, prior to extraction, a wet-heat treatment.

According to one particularly preferred embodiment, the extract is an extract of rye flakes.

The cereal extract is advantageously prepared by bringing the cereal or the cereal fraction that has been selected into contact with a polar solvent or a mixture of polar solvents.

As a polar solvent that can be used for the extraction step, a solvent or a mixture of solvents is advantageously chosen from water, a $C_1$-$C_4$ alcohol, for example ethanol, and a $C_2$ to $C_6$ glycol preferably chosen from glycerol, butylene glycol and propylene glycol, and mixtures thereof.

According to one particular embodiment, the above-mentioned extract is an aqueous extract or an extract obtained by extraction in an aqueous-alcoholic or aqueous-glycolic solution containing at least 50% v/v of water.

According to one particularly preferred variant, the preparation process is in accordance with that described in French patent application FR 2 893 504, the content of which is included in the present application by way of reference.

Thus, the cereal extract according to the invention is advantageously prepared by means of a process that can advantageously comprise the succession of following steps:
- suspension of the cereal or of parts of cereals in water,
- simultaneous or successive enzymatic hydrolysis or hydrolyses,
- separation of the soluble and insoluble phases by filtration, centrifugation, settling out,
- heat treatment,
- purification of the active fraction by filtration, and
- sterilizing filtration.

According to one preferred variant of the invention, the cereal extract is particularly rich in saccharide compounds such as one or more of glucose, xylose, xylan, and derivatives thereof.

According to yet another preferred variant of the invention, the extract comprises at least 90% by weight of total sugars, preferably at least 95% by weight of total sugars, the percentage being expressed relative to the solids constituting the extract.

According to a second aspect, the present invention is also directed toward a cosmetic composition with slimming activity, characterized in that it comprises one or more slimming agents, wherein at least one slimming agent is a cereal extract rich in saccharide compounds, obtained by means of at least one polar solvent, said extract being as defined above or as results from the following description taken as a whole.

According to one particular embodiment of the composition, said composition is characterized in that the concentration of cereal extract is between 0.0001% and 1% by weight, in particular between 0.01% and 0.5% by dry weight of extract, relative to the weight of the cosmetic composition.

The composition according to the invention may also advantageously comprise one or more other cosmetic active agents which have cosmetic effects similar and/or complementary to those of the invention.

The advantageous active agents may in particular be chosen from those which have a slimming effect through an action on lipogenesis, on lipolysis or on lipid storage, for example by acting on the intracellular level of cyclic adenosine 3',5'-monophosphate (cyclic AMP or cAMP), those which act on factors responsible for the appearance of cellulite, such as the infiltration of water in the tissues, and those which have a restructuring effect and which act to preserve tissue firmness, by protecting the extracellular matrix.

The composition according to the invention may thus comprise phytosphingosine or a cosmetically acceptable salt thereof, in particular the hydrochloride thereof, preferably at a concentration of between 0.001% and 1%, and preferably between 0.05% and 0.5% by weight, relative to the total weight of said composition.

The composition according to the invention may also comprise one or more active agents chosen from the group consisting of cAMP and derivatives thereof, agents which activate the adenylate cyclase enzyme and agents which inhibit the phosphodiesterase enzyme.

As cAMP derivative, any cosmetically acceptable cAMP derivative, and in particular a salt or an acylated derivative, especially a monobutyryl or dibutyryl derivative, may be chosen.

In these cosmetic compositions, the cAMP or derivative thereof is advantageously used at a concentration of between 0.001% and 5% by weight, relative to the total weight of the composition.

As adenylate cyclase-activating agent, forskolin or a plant extract containing same is advantageously chosen, preferably at a concentration of between 0.001% and 1%, and preferably between 0.05% and 0.25% by weight, relative to the total weight of the composition.

As forskolin-containing extract, an extract of *Coleus forskholii*, in particular a bark extract of said plant, is preferably chosen. Such an extract can be obtained by means of an extraction process such as that described in European patent EP 486595 B1.

An extract of the plant *Tephrosia purpurea*, in particular a seed extract of this plant, may also be used as adenylate cyclase-activating agent, at a concentration of between 0.001% and 5%, preferably between 0.01% and 5% by weight, relative to the total weight of the composition. Such an extract is, for example, obtained by means of an extraction process described in European patent EP 711141 B1.

As phosphodiesterase-inhibiting agent, use may be made of a xanthine such as 3-isobutyl-1-methylxanthine or IBMX, caffeine or theophilline, preferably at a concentration of between 0.001% and 10%, and more preferably between 0.01 and 1% by weight, relative to the weight of the composition.

The composition according to the invention may also comprise active agents chosen from an extract of *Cola acuminata*, linoleic acid, an extract of *Vitis vinifera*, glycosphingolipids, dihydromyricetin, hexapeptide-11, a mixture of a hydrolyzed extract of *Prunella vulgaris* and of a hydrolyzed extract of *Celosia cristata*, an extract of *Anogeissus leiocarpus*, in particular a bark extract of said plant, a leaf extract of *Manihot utllissima*, madecassoside or a plant extract containing same, a vitamin A ester, in particular retinyl palmitate, sericoside or a plant extract containing same, N-acetyl-dipeptide-1-hexadecyl ester, and an extract of *Visnaga Vera*.

The compositions according to the invention also comprise at least one cosmetically acceptable excipient which may be in particular chosen from pigments, coloring agents, polymers, surfactants, rheological agents, fragrances, electrolytes, pH adjusters, antioxidants and preservatives, and mixtures thereof.

The cosmetic composition according to the invention may, for example, be in the form of a serum, a lotion, an emulsion, for example a cream, or alternatively a hydrogel, or be in the form of a stick or a patch.

According to a third aspect, the present invention is also directed toward a slimming cosmetic care method, characterized in that it comprises the topical application, to a relevant area of the body skin, of a slimming cosmetic composition comprising at least one cereal extract, said composition being as defined above or as results from the following description taken as a whole.

It is thus understood that the invention indeed solves the new technical problem stated above by providing a novel slimming agent using a renewable natural source, in a manner which is simple and inexpensive and can be used on the industrial and cosmetic scale.

EXAMPLE 1

Preparation of a Rye Extract According to the Invention

An extract is prepared from flakes obtained from the seeds of the *Secale cereale* (rye) plant by means of a steam treatment.

The extraction process advantageously comprises the following steps:

suspension of the rye flakes in water, enzymatic hydrolysis, separation of the soluble and insoluble phases, heat treatment, purification and sterilizing filtration.

At the end of the extraction process, an aqueous solution of rye extract comprising approximately 5% by weight of solids is obtained.

EXAMPLE 2

Modulatory Effects of Active Agents on α5 Integrin Expression in Adipocytes

3T3-F442A preadipocytes are cultured on slides, onto which fibronectin has been run so as to promote adhesion and cell proliferation (Kuwada S K et al., *Mol Biol Cell.* 2000 July; 11(7):2485-96; Sastry S K et al, *J Cell Biol.* 1999 Mar. 22; 144(6): 1295-309).

The expression of the α5 integrins is characterized by immunofluorescence on 3T3-F442A preadipocytes treated with an aqueous rye extract obtained according to example 1. The various labelings are visualized with a confocal microscope and then the fluorescence corresponding to the presence of the α5 integrins at the cell surface is quantified by image analysis.

Materials and Methods

1—Reagent

Dulbecco's modified Eagle's minimum essential medium (DMEM)+4.5 g/l of glucose: INVITROGEN calf serum (CS): BIOWEST PBS (DPBS+$CaCl_2$+$MgCl_2$ GIBCO 14040-091)

BSA: bovine serum albumin SIGMA

10% formalin, solution of formaldehyde at 4% (SIGMA)

anti-α5-integrin antibody (SANTA CRUZ BIOTECHNOLOGY)

goat anti-rabbit antibody coupled to Alexa fluor 546 (INVitrogen, Molecular Probes)

SYTOXGREEN: (nucleic acid stain, 5 mM stock solution in DMSO, Molecular Probes). Final dilution $\frac{1}{20000}$, i.e. first dilution in PAB to $\frac{1}{100}^{th}$, then $\frac{1}{200}^{th}$ with the solution for preparing the second antibody.

slides coated with fibronectin: BIOCOAT CELLWARE, HUMAN FIBRONECTIN 4 WELLS (FALCON).

2—Cell Culture

A clone which accumulates large amounts of triglycerides in the resting state is isolated from an established mouse fibroblast line 3T3. These murine preadipocytes (3T3-F442A) (Green H. and Kehinde O. *Cell.* 1976; 7(1):105-13) can multiply and differentiate, giving the morphological and biochemical phenotype characteristic of the differentiated function of the mature adipocyte. When they are in the exponential growth phase, they have a fibroblast appearance, with an elongated shape, and are very adherent to the support.

The 3T3-F442A preadipocytes are seeded onto 4-well Labtek slides coated with fibronectin, at a rate of $2 \times 10^3$ cells per well, in 1 ml of medium, and placed in the incubator at 37° C. under an air-$CO_2$ (95-5%) atmosphere. The cells are cultured in DMEM medium (4.50 g/l glucose), supplemented with 10% calf serum (CS) for 48 hours, and then treated with the active agent in this same medium.

3—Treatment

The cells are treated in the wells for 24 hours.

The rye extract prepared in example 1 is tested diluted to 0.05% by weight of solids in the culture medium.

4—α5 Integrin Immunolabeling

At the end of the treatment, the cells are rinsed in PBS with calcium and magnesium and then in formalin and fixed with formalin for 20 minutes at ambient temperature. The cells are then rinsed with PBS-BSA (PAB) 3% (cf. appendix I) and brought into contact with a solution of PAB 3% for 1 hour. The slides are dried and then incubated for 1 hour, at ambient temperature, with the antibody directed against α5 integrin, diluted to $\frac{1}{50}^{th}$ in the PAB 3%. After two rinses, each for 15 minutes, and two baths, each for 15 minutes, in PAB, the slides are dried and then incubated for 45 minutes with the anti-rabbit antibody coupled to Alexa fluor 546, diluted to $\frac{1}{200}^{th}$ in PAB. The cell nuclei are stained with Sytoxgreen (dilution to $\frac{1}{200}^{th}$ in the above solution). After two rinses, each for 15 minutes, and two baths, each for 15 minutes, in PAB, the slides are dried and mounted between slides and cover slips.

The observations are made on a confocal microscope (BIORAD MRC 1024) and the acquisition of ten images on ten different areas of the culture medium is carried out by means of the LaserSharp 2000 software (BIORAD) for the control and the treated sample. Four images taken randomly among the ten images illustrate the invention in FIGS. 1 (nontreated control) and 2 (treatment with the extract of the invention).

Figure 2:
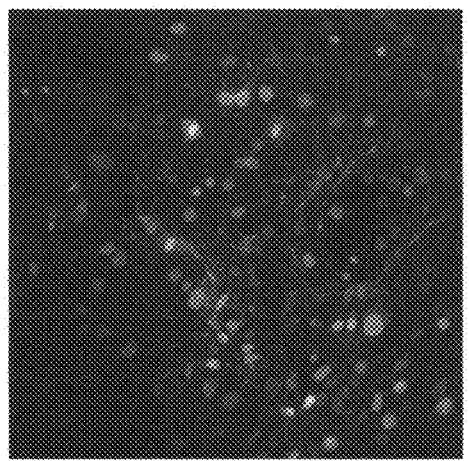
FIG. 2 also represents four images taken on four different areas of the culture medium of cells treated with an aqueous extract of rye diluted to approximately 0.05% by weight of solids in the culture medium, for observation of the expression of α5 integrins at the surface of the treated cells.
Figure 2:
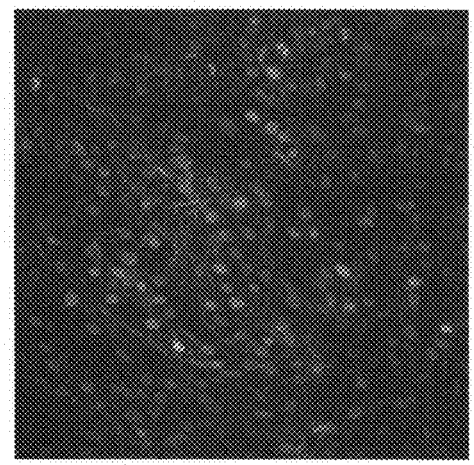
Figure 2:
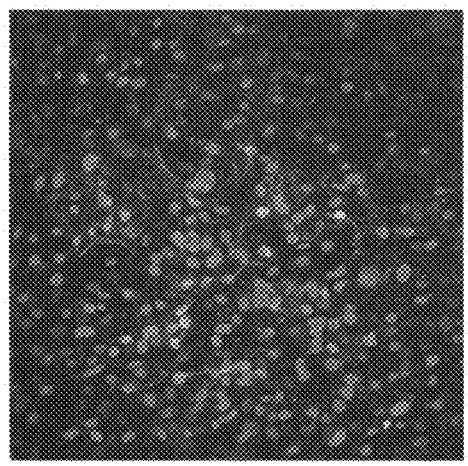
Figure 2:
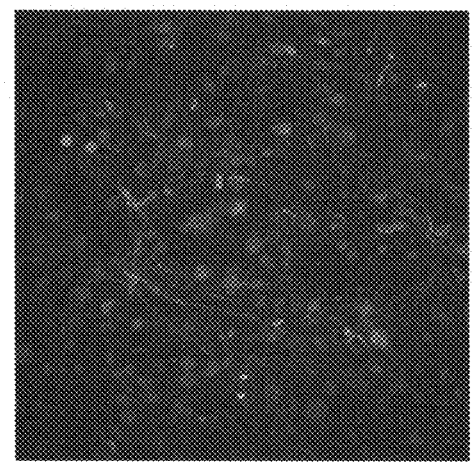

The fluorescences (red for the α5-integrin network and green for the staining of the nuclei) are analyzed and the labeling is quantified by means of the LEICA QWIN V3 software according to the following steps:

step 1: the image resulting from the combination of the original photos represents the α5-integrin labeling in red and the labeling of the cell nuclei in green;

step 2: the image analysis software detects the pixels positive for the α5-integrin labeling. The measurement is carried out on the number of red pixels detected, which corresponds to the amount of α5-integrin present in each cell;

step 3: the software detects the green pixels corresponding to the cell nuclei. The measurement is carried out on the number of objects;

step 4: the area of measurement is made up of the entire microscopic field represented in the attached FIG. 1 or 2.

The action of the rye extract obtained according to example 1, tested at 0.05% by weight of solids, on the strength of α5-integrin labeling is evaluated. The total labeling of α5-integrin in the preadipocytes is measured, said labeling subsequently being standardized relative to the number of nuclei counted in the measurement area.

Results:

The results after treatment are indicated in the table below.

| Treatment | Alpha 5 labeling | alpha 5 labeling/ no. of nuclei |
|---|---|---|
| Nontreated control (NTC) | 3256 (+/−1308) | 10.38 (+/−3.53) |
| 0.05% rye extract | 14877 (+/−4065)$^s$ | 52.00 (+/−11.84)$^s$ |

The $^S$ indicate a significant difference with the control (value of p ≤ 0.05).

Conclusions:

The images taken on the confocal microscope reveal punctate surface labeling which gets stronger after treatment of the cells with the rye extract. The appearance changes, the arrangement of the fluorescence is modified, to be replaced by a more fibrous structure with the treatment.

The quantification indicates an increase in the fluorescence of approximately 80% between the nontreated control cells and the cells treated with the dilute solution of rye extract.

The ANOVA statistical test indicates a significant difference on the strength of the α5-integrin labeling between the nontreated controls and the cells treated with the rye extract.

The preadipocytes cultured in the presence of the rye extract in accordance with the invention and prepared according to example 1 express more α5-integrin, which reinforces their ability to maintain the cells in a non-adipocyte state: after treatment, the cells enjoy conditions that are less favorable to their entry into cell differentiation.

EXAMPLE 3

Slimming Cosmetic Compositions

A slimming body cream comprising a rye extract, in the form of an aqueous solution in which the extract is diluted to approximately 0.05% by weight of solids, is prepared.

The cosmetic composition is an oil-in-water emulsion such as those skilled in the art know how to prepare (percentages expressed by weight relative to the final composition).

| | % |
|---|---|
| Rye extract | 0.1 |
| Seed extract of *Tephrosia purpurea* | 1 |
| Excipients for cream | qs 100 |

The composition is applied daily, for 2 to 3 weeks, to the areas of the body requiring the use thereof, until the desired slimming effect is obtained.

The invention claimed is:

1. A slimming method using a slimming topical composition comprising: applying the slimming topical composition to an area of skin in need thereof, wherein the slimming topical composition comprises an effective amount to provide a slimming effect of at least one cereal extract comprising a rye extract, and wherein the cereal extract comprises at least 90% by weight of total sugars, the percentage being expressed relative to solids constituting the cereal extract.

2. The method as claimed in claim 1, wherein said cereal extract is obtained by extraction with at least one polar solvent.

3. The method as claimed in claim 1, wherein the cereal extract is obtained from all or part of the rye alone or as a mixture with at least one other cereal.

4. The method as claimed in claim 3, wherein the other cereal is selected from the group consisting of wheat, barley, and oats.

5. The method as claimed in claim 3, wherein the cereal comprises saccharide compounds.

6. The method as claimed in claim 1, wherein the cereal comprises saccharide compounds.

7. The method as claimed in claim 1, wherein the cereal comprises at least one compound selected from the group consisting of: xylan, arabinoxylan, glucose, and xylose.

8. The method as claimed in claim 1, wherein the cereal comprises arabinoxylan.

9. The method as claimed in claim 1, wherein the cereal extract is obtained from at least one cereal fraction chosen from the group consisting of fibers, fibers contained in the stalks; fibers contained in the leaves, fibers contained in the seeds, fibers contained in the hulls, fibers contained in the bran of cereals.

10. The method as claimed in claim 1, wherein the cereal extract is obtained from flakes of said cereal.

11. The method as claimed in claim 1, wherein the rye extract is an extract of rye flakes.

12. The method as claimed in claim 1, wherein the cereal extract is a rye extract prepared by bringing the rye or a rye part into contact with a polar solvent or a mixture of polar solvents.

13. The method as claimed in claim 1, wherein said cereal extract is obtained by extraction with a polar solvent or a mixture of polar solvents selected from the group consisting of: water, a $C_1$-$C_4$ alcohol, a $C_2$ to $C_6$ glycol, and any mixtures thereof.

14. The method of claim 13, wherein the alcohol is ethanol; and the glycol is selected from the group consisting of glycerol, butylene glycol, propylene glycol and any mixture thereof.

15. The method as claimed in claim 1, wherein the cereal extract is an aqueous extract or an extract obtained by extraction in an aqueous-alcoholic or aqueous-glycolic solution comprising at least 50% v/v of water.

16. The method as claimed in claim 1, wherein the cereal extract is prepared by means of a method comprising the succession of following steps:
   suspension of the cereal comprising rye or of parts of cereal comprising rye in water;
   simultaneous or successive enzymatic hydrolysis or hydrolyses;
   separation of the soluble and insoluble phases by filtration, centrifugation, or settling out to provide an active fraction;
   heat treatment;
   purification of the active fraction by filtration; and
   sterilizing filtration.

17. The method as claimed in claim 1, wherein the cereal extract comprises at least 95% by weight of total sugars, and the percentage being expressed relative to the solids constituting the cereal extract.

18. A slimming method using a slimming topical composition comprising: applying the slimming topical composition to an area of skin in need thereof, wherein the slimming topical composition comprises between 0.01% and 0.5% by dry weight of at least one cereal extract comprising a rye extract, relative to the weight of the cosmetic composition, and wherein the cereal extract comprises at least 90% by weight of total sugars, the percentage being expressed relative to solids constituting the cereal extract.

19. A slimming method using a slimming topical composition comprising: topically applying between 0.0001% and 1% by weight, relative to the weight of the cosmetic composition, of at least one cereal extract comprising a rye extract to an area of skin in need thereof, and at least one additional cosmetically active agent selected from the group consisting of: an additional slimming agent having a slimming effect through an action on lipogenesis, lipolysis or lipid storage; an additional agent acting on factors responsible for the appearance of cellulite; an additional agent having a skin restructuring effect and acting to preserve tissue firmness by protecting the extracellular matrix; a phytosphingosine or a cosmetically acceptable salt thereof; a cAMP component select from cAMP, a cAMP salt, and acylated cAMP; an additional agent activating adenylate cyclase enzyme; an agent inhibiting phosphodiesterase enzyme; an extract of *Cola acuminata*, linoleic acid, an extract of *Vitis vinifera*, a glycosphingolipid, dihydromyricetin, hexapeptide-11, a mixture of a hydrolyzed extract of *Prunella vulgaris* and *Celosia cristata*; an extract of *Anogeissus leiocarpus*, a leaf extract of *Manihot utilissima*, madecassoside or a plant extract containing madecassoside; a vitamin A ester; sericoside or a plant extract containing a sericoside; N-acetyl-dipeptide-1-hexadecyl ester; and an extract of *Visnaga vera*.

20. The method of claim 19, wherein acylated cAMP is selected from the group consisting of monobutyryl cAMP, and dibutyryl cAMP.

21. The method of claim 19, comprising applying a cosmetic composition comprising said cereal extract and said additional cosmetically active agent, wherein said cAMP component is at a concentration ranging between 0.001% and 5% by weight, relative to the total weight of said cosmetic composition.

22. The method of claim 19, wherein said adenylate cyclase-activating agent is selected from the group consisting of forskolin, a plant extract containing forskolin, and an extract of *Coleus forskholii*.

23. The method of claim 22, comprising applying a cosmetic composition comprising said cereal extract and said adenylate cyclase-activating agent at a concentration ranging between 0.001% and 1% by weight relative to the total weight of said cosmetic composition.

24. The method of claim 19, wherein said adenylate cyclase-activating agent is an extract of *Tephrosia purpurea*.

25. The method of claim 24, comprising applying a cosmetic composition comprising said cereal extract and said extract of *Tephrosia purpurea* at a concentration ranging between 0.001% and 5% by weight relative to the total weight of said cosmetic composition.

26. The method of claim 19, wherein said phosphodiesterase-inhibiting agent comprises a xanthine.

27. The method of claim 26, wherein said xanthine is selected from the consisting of 3-isobutyl-1-methylxanthine, caffeine and theophylline.

28. The method of claim 26, further comprising applying a cosmetic composition comprising said cereal extract, and said xanthine at a concentration ranging between 0.001% and 10% relative to the weight of said cosmetic composition.

29. The method of claim 19, wherein said vitamin A ester is vitamin A retinyl palmitate.

30. A method for slimming an area of skin comprising: topically applying a slimming composition comprising between 0.001 and 1% by weight relative to the total weight of said cosmetic composition of a rye extract, and between 0.001 and 5% by weight relative to the total weight of said cosmetic composition of an extract of *Tephrosia purpurea* on an area of skin in need thereof.

31. The method of claim 30, wherein the slimming composition comprises about 0.1 weight % of rye extract and about 1% of an extract of seeds of *Tephrosia purpurea*.

32. A method for slimming an area of skin comprising topically applying a slimming composition to an area of skin in need thereof, wherein the slimming composition comprises at least one cereal extract, comprising a rye extract, in an amount of between 0.0001% and 1% by weight, relative to the weight of the composition, and wherein the cereal extract comprises at least 90% by weight of total sugars, the percentage being expressed relative to solids constituting the cereal extract.

33. The method of claim 32, wherein said cereal extract is a rye extract.

* * * * *